(12) United States Patent
Saunders et al.

(10) Patent No.: US 7,645,409 B2
(45) Date of Patent: Jan. 12, 2010

(54) POLYMER LINK HYBRID STENT

(75) Inventors: Richard J. Saunders, Redwood City, CA (US); Joseph R. Callol, San Francisco, CA (US); James Hong, Santa Clara, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 0 days.

(21) Appl. No.: 12/245,420

(22) Filed: Oct. 3, 2008

(65) Prior Publication Data
US 2009/0029030 A1    Jan. 29, 2009

Related U.S. Application Data

(62) Division of application No. 10/334,035, filed on Dec. 30, 2002, now Pat. No. 7,455,687.

(51) Int. Cl.
*B29C 45/14*    (2006.01)

(52) U.S. Cl. .................... 264/279; 264/271.1; 264/259

(58) Field of Classification Search ............ 264/271.1, 264/279
See application file for complete search history.

(56) References Cited

U.S. PATENT DOCUMENTS

| | | | |
|---|---|---|---|
| 4,323,071 A | 4/1982 | Simpson et al. |
| 4,439,185 A | 3/1984 | Lundquist |
| 4,516,972 A | 5/1985 | Samson |
| 4,538,622 A | 9/1985 | Samson et al. |
| 4,554,929 A | 11/1985 | Samson et al. |
| 4,616,652 A | 10/1986 | Simpson |
| 4,638,805 A | 1/1987 | Powell |
| 4,665,906 A | 5/1987 | Jervis |
| 4,748,982 A | 6/1988 | Horzewski et al. |
| 4,925,445 A | 5/1990 | Sakamoto et al. |
| 4,989,608 A | 2/1991 | Ratner |
| 5,154,179 A | 10/1992 | Ratner |
| 5,163,952 A | 11/1992 | Froix |

(Continued)

FOREIGN PATENT DOCUMENTS

DE    197 28 337 A1    1/1999

(Continued)

OTHER PUBLICATIONS

Duerig, T.W., et al., *Engineering Aspects of Shape Memory Alloys*, Butterworth-Heinemann Ltd., 1990.

(Continued)

*Primary Examiner*—Joseph S. Del Sole
*Assistant Examiner*—James Sanders
(74) *Attorney, Agent, or Firm*—Fulwilder Patton LLP (57) ABSTRACT

The present invention is directed to an expandable polymer link hybrid stent for implantation in a body lumen, such as a coronary artery along with a method of making the stent. The stent generally includes a series of metallic cylindrical rings longitudinally aligned on a common axis of the stent and interconnected by a series of polymeric links. The polymer links are formed by applying polymer layers between the rings and laser ablating the excess material. The polymeric material forming the polymeric links, provides longitudinal and flexural flexibility to the stent while maintaining sufficient column strength to space the cylindrical rings along the longitudinal axis. The metallic material forming the rings provides the necessary radial stiffness.

11 Claims, 7 Drawing Sheets

U.S. PATENT DOCUMENTS

| | | | |
|---|---|---|---|
| 5,591,224 | A | 1/1997 | Schwartz et al. |
| 5,603,722 | A | 2/1997 | Phan et al. |
| 5,653,727 | A | 8/1997 | Wiktor |
| 5,690,644 | A | 11/1997 | Yurek et al. |
| 5,716,393 | A | 2/1998 | Lindenberg et al. |
| 5,728,079 | A | 3/1998 | Weber et al. |
| 5,779,729 | A | 7/1998 | Severini |
| 5,800,526 | A | 9/1998 | Anderson et al. |
| 5,836,964 | A | 11/1998 | Richter et al. |
| 5,837,313 | A | 11/1998 | Ding et al. |
| 5,843,172 | A | 12/1998 | Yan |
| 5,908,410 | A | 6/1999 | Weber et al. |
| 6,004,348 | A | 12/1999 | Banas et al. |
| 6,013,854 | A | 1/2000 | Moriuchi |
| 6,053,941 | A | 4/2000 | Lindenberg et al. |
| 6,139,573 | A | 10/2000 | Sogard et al. |
| 6,143,022 | A | 11/2000 | Shull et al. |
| 6,156,064 | A | 12/2000 | Chouinard |
| 6,179,817 | B1 | 1/2001 | Zhong |
| 6,245,099 | B1 | 6/2001 | Edwin et al. |
| 6,251,136 | B1 | 6/2001 | Guruwaiya et al. |
| 6,315,788 | B1 | 11/2001 | Roby |
| 6,325,824 | B2 | 12/2001 | Limon |
| 6,338,740 | B1 | 1/2002 | Carpentier |
| 6,340,367 | B1 | 1/2002 | Stinson et al. |
| 6,380,457 | B1 | 4/2002 | Yurek et al. |
| 6,383,216 | B1 | 5/2002 | Kavteladze et al. |
| 6,409,754 | B1 | 6/2002 | Smith et al. |
| 6,520,986 | B2 | 2/2003 | Martin et al. |
| 6,565,599 | B1 | 5/2003 | Hong et al. |
| 6,755,855 | B2 | 6/2004 | Yurek et al. |
| 6,805,705 | B2 * | 10/2004 | Hong et al. ................ 623/1.15 |
| 2001/0025130 | A1 | 9/2001 | Tomonto |
| 2002/0007102 | A1 | 1/2002 | Salmon et al. |
| 2002/0151964 | A1 | 10/2002 | Smith et al. |
| 2005/0107864 | A1 * | 5/2005 | Hong et al. ................ 623/1.15 |

FOREIGN PATENT DOCUMENTS

| | | |
|---|---|---|
| EP | 0 480 667 A1 | 4/1992 |
| WO | WO 96/39103 | 12/1996 |
| WO | WO 98/20810 | 5/1998 |
| WO | WO 01/01888 | 1/2001 |
| WO | WO 02/053066 A1 | 7/2002 |

OTHER PUBLICATIONS

Wang, GE, *Welding of Nitinol to Stainless Steel*, Proceedings of the Second International Conference on Shape Memory and Superelastic Technologies, pp. 131-136, 1997.

U.S. Appl. No. 09/848,818 to Au et al., filed May 3, 2001.
U.S. Appl. No. 09/897,719 to Jackson et al., filed Jun. 29, 2001.
U.S. Appl. No. 10/014,052 to McQuiston et al., filed Dec. 10, 2001.
U.S. Appl. No. 10/032,939 to Hong et al., filed Dec. 26, 2001.
U.S. Appl. No. 10/033,380 to Hong et al., filed Dec. 27, 2001.
U.S. Appl. No. 10/035,037 to Cox, filed Dec. 28, 2001.

* cited by examiner

POLYMER LINK HYBRID STENT

This application is a divisional of U.S. Ser. No. 10/334,035 filed Dec. 30, 2002.

BACKGROUND OF THE INVENTION

This invention relates to expandable endoprosthesis devices, generally called stents, which are adapted to be implanted into a patient's body lumen, such as blood vessel, to maintain the patency thereof. These devices are useful in the treatment of atherosclerotic stenosis in blood vessels.

Stents are generally tubular-shaped devices which function to hold open a segment of a blood vessel, coronary artery, or other anatomical lumen.

Various means have been described to deliver and implant stents. One method frequently described for delivering a stent to a desired intraluminal location includes mounting the expandable stent on an expandable member, such as a balloon, provided on the distal end of an intravascular catheter, advancing the catheter to the desired location within the patient's body lumen, inflating the balloon on the catheter to expand the stent into a permanent expanded condition and then deflating the balloon and removing the catheter. One of the difficulties encountered using prior stents involved maintaining the radial rigidity needed to hold open a body lumen while at the same time maintaining the longitudinal flexibility of the stent to facilitate its delivery. Once the stent is mounted on the balloon portion of the catheter, it is often delivered through tortuous vessels, including tortuous coronary arteries. The stent must have numerous properties and characteristics, including a high degree of flexibility in order to appropriately navigate the tortuous coronary arteries. This flexibility must be balanced against other features including radial strength once the stent has been expanded and implanted in the artery. While other numerous prior art stents have had sufficient radial strength to hold open and maintain the patency of a coronary artery, they have lacked the flexibility required to easily navigate tortuous vessels without damaging the vessels during delivery.

Generally speaking, most prior art intravascular stents are formed from a metal such as stainless steel, which is balloon expandable and plastically deforms upon expansion to hold open a vessel. The component parts of these types of stents typically are all formed of the same type of metal, i.e., stainless steel. Other types of prior art stents may be formed from a polymer, again all of the component parts being formed from the same polymer material. These types of stents, the ones formed from a metal and the ones formed from a polymer, each have advantages and disadvantages. One of the advantages of the metallic stents is their high radial strength once expanded and implanted in the vessel. A disadvantage may be that the metallic stent lacks flexibility which is important during the delivery of the stent to the target site. With respect to polymer stents, they may have a tendency to be quite flexible and are advantageous for use during delivery through tortuous vessels, however, such polymer stents may lack the radial strength necessary to adequately support the lumen once implanted.

What has been needed and heretofore unavailable is a stent which has a high degree of flexibility so that it can be advanced through tortuous passageways and can be readily expanded and yet have the mechanical strength to hold open the body lumen into which it expanded. The present invention satisfied these needs.

SUMMARY OF THE INVENTION

The present invention is directed to an expandable hybrid stent for implantation in a body lumen, such as a coronary artery and a method of making the same. The stent generally consists of a series of metallic cylindrical rings used in connection with a series of polymeric links and in some cases a polymeric coating. The cylindrical rings are radially expandable and longitudinally aligned along a common axis of the stent. The rings are interconnected by one or more of the polymeric links and both the rings and links may be coated with the polymeric coating. The polymeric material forming the links provides longitudinal and flexural flexibility to the stent while maintaining sufficient column strength to space the cylindrical rings along the longitudinal axis, the metallic material forming the rings provides the necessary radial stiffness after the stent is implanted into a body lumen, and the polymeric coating may provide further structural integrity.

In the case of a balloon expandable catheter system the cylindrical rings and the polymeric links remain closely coupled from the time the stent is crimped onto the delivery system to the time the stent is expanded and implanted into a body lumen. Accordingly, both the cylindrical rings and the polymeric links have first delivery diameters in the crimped state of the stent and second larger implanted diameters in the expanded state of the stent.

The metallic cylindrical rings can have undulations including peaks and valleys generally formed as U- and W-shaped members. The peaks of each cylindrical ring can be axially aligned with the valleys of each adjacent cylindrical ring to provide the desired flexibility or vice versa to provide rigidity. The resulting stent structure is a series of radially expandable cylindrical rings which are spaced longitudinally close enough to adequately cover the wall of a body lumen, but not so close as to compromise the longitudinal flexibility of the stent.

The metallic cylindrical rings can be interconnected with a series of polymeric links through a variety of connection types including anchoring mechanisms, bonding agents and coatings. The polymeric links provide flexibility and allow the stent to easily bend or flex along its longitudinal axis as the stent navigates through tortuous vessels or coronary arteries. The polymer links also provide a good platform for a drug coating. The combination of the flexible metallic cylindrical rings when used in connection with the polymeric links cumulatively provide a stent which is flexible along its length and about its longitudinal axis, yet is still relatively stiff in the radial direction after it is expanded in order to maintain the patency of a vessel and to resist collapse.

The stent embodying features of the invention can be readily delivered to the desired body lumen, such as a coronary artery (peripheral vessels, bile ducts, etc.), by mounting the stent on an expandable member of a delivery catheter, for example a balloon, and advancing the catheter and stent assembly through the body lumen to the target site. Generally, a crimping tool is used to crimp the stent onto the balloon portion of the catheter so that the stent does not move longitudinally relative to the balloon portion of the catheter during delivery through the arteries, and during expansion of the stent at the target site. During the crimping process the metallic cylindrical rings undergo a plastic deformation and radially compress.

After insertion of the stent to the desired location of delivery, the balloon is inflated to implant the stent. The metallic cylindrical rings of the stent are plastically deformed when expanded so that the stent will remain in the expanded condition and therefore they must be sufficiently rigid when expanded to prevent the collapse thereof in use. During expansion of the stent, portions of the cylindrical rings may tip outwardly resulting in projecting members on the outer surface of the expanded stent. These projecting members may tip radially outwardly from the outer surface of the stent and may embed into the vessel wall and help secure the expanded stent once it is implanted.

In one method of manufacturing the stent, a solution is first prepared using a biocompatible polymer and solvent. A mandrel with laser registration features is then coated with the solution to build a thickness approximately equivalent to the thickness of stent rings. The mandrel is placed in a laser rotary fixture where the laser is then used to cut a female pattern of the stent rings into the polymer coatings. The mandrel is then removed from the laser rotary fixture with its position registered in control memory. The stent rings are thereafter embedded into the conforming ring-cavities in the polymeric coating. A second coating is applied to the assembly until the desired coating thickness is achieved. Once cured, the assembly is placed back into the laser rotary fixture, and the polymer coating lining the perimeter of the desired stent profile is ablated to form the finished stent.

It is to be recognized that the stent of the present invention can be self-expanding or balloon-expanded and made by other processes. Moreover, the stent of the present invention can be modified to be used in other body lumens including highly tortuous and distal vasculature as well as to create whole or portions of other medical devices or markers placed on such devices.

Other features and advantages of the present invention will become more apparent from the following detailed description of the invention when taken in conjunction with the accompanying exemplary drawings.

DETAILED DESCRIPTION OF THE PREFERRED EMBODIMENTS

Figure 1:
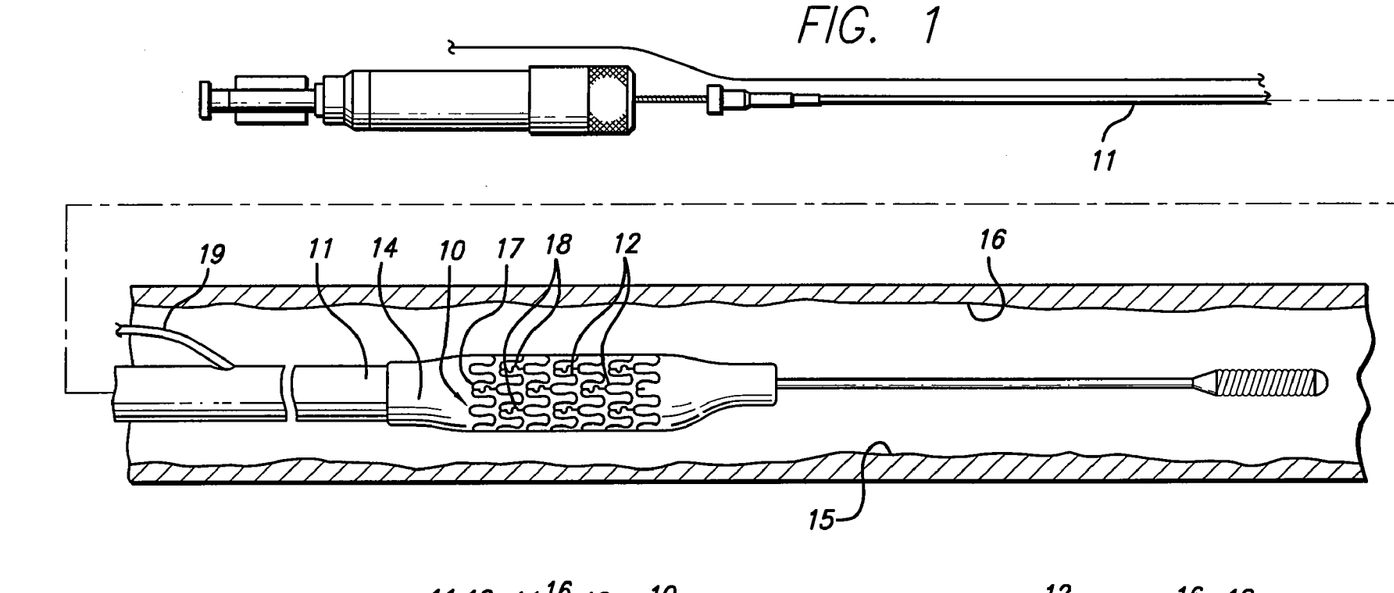
FIG. 1 is an elevational view, partially in section, of a stent embodying features of the invention which is mounted on a delivery catheter and disposed within an artery.

Before describing in detail an exemplary embodiment of a hybrid stent with polymeric and metallic components in accordance with the present invention, it is instructive to briefly describe a typical stent implantation procedure and the vascular conditions which are typically treated with stents. Referring now to FIG. 1, a stent 10 of the present invention is shown mounted on a catheter 11 having a lumen 19 and an inflation member (balloon) 14. The stent and catheter are shown inside the lumen of an arterial vessel 16. The stent is shown positioned across a small amount of arterial plaque 15 adhering to the lumen of the artery. In some procedures, a stent is directly implanted without a prior procedure, such as balloon angioplasties. In other procedures, the plaque is remodeled when it is radially compressed against the walls of the artery, or has been partially removed from the artery. Lesion dilation is typically accomplished by an angioplasty procedure, while lesion removal is typically accomplished by an atherectomy procedure. These and other procedures for the treatment of arterial lesions are well known to those skilled in the art.

With most lesion treatment procedures, the treated artery suffers a degree of trauma, and in a certain percentage of cases may abruptly collapse or may slowly narrow over a period of time due to neointimal hyperplasia which is referred to as restenosis. To prevent either of these conditions, the treated artery is often fitted with a prosthetic device, such as the stent 10 of the present invention. The stent provides radial support for the treated vessel and thereby prevents collapse of the vessel 16, and further provides scaffolding to prevent plaque prolapse within the lumen. The stent may also be used to repair an arterial dissection, or an intimal flap, both of which are sometimes found in the coronary arteries, peripheral arteries and other vessels. In order to perform these functions, the stent must be accurately placed across the lesion site. Therefore, it is critical that the stent be sufficiently radiopaque so that the physician can visually locate the stent under fluoroscopy during the implantation procedure. However, it is equally important that the stent not be too radiopaque. If the stent is overly radiopaque, i.e., too bright, the physician's view of the lumen is compromised. This makes assessment of subsequent restenosis difficult. In cases where the balloon markers are very close to the stent, the stent can blend in with the markers. Without precise visualization of the stent ends, accurate placement of the stent in a lesion, particularly in the case of an ostial lesion, can be compromised.

With continued reference to FIG. 1, in a typical stent placement procedure, a guiding catheter (not shown) is percutaneously introduced into the cardiovascular system of a patient through the femoral arteries by means of a conventional Seldinger technique, and advanced within a patient's vascular system until the distal end of the guiding catheter is positioned at a point proximal to the lesion site. A guide wire and the stent-delivery catheter 11 of the rapid exchange type are introduced through the guiding catheter with the guide wire sliding within the stent-delivery catheter. The guide wire is first advanced out of the guiding catheter into the arterial vessel 16 and is advanced across the arterial lesion. Prior to implanting the stent, the cardiologist may wish to perform an angioplasty or other procedure (e.g., atherectomy) in order to open and remodel the vessel and the diseased area. An over the wire catheter (not shown) also can be used to deliver the stent of the invention.

Figure 2:
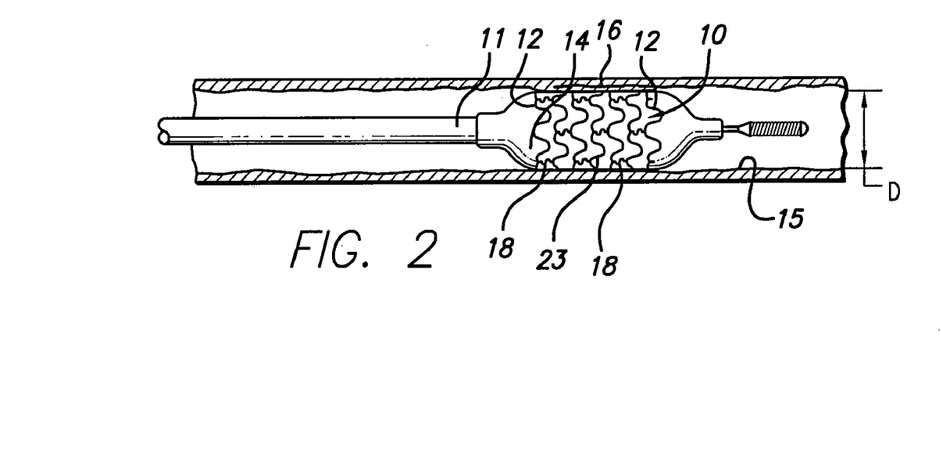
FIG. 2 is an elevational view, partially in section, similar to that shown in FIG. 1 wherein the stent is expanded within an artery.

Referring to FIG. 2, the stent delivery catheter assembly 11 is advanced over the guide wire so that the stent 10 is positioned in the target area. The stent-delivery catheter is subsequently advanced over the previously positioned guide wire until the stent is properly positioned across the lesion.

Figure 3:
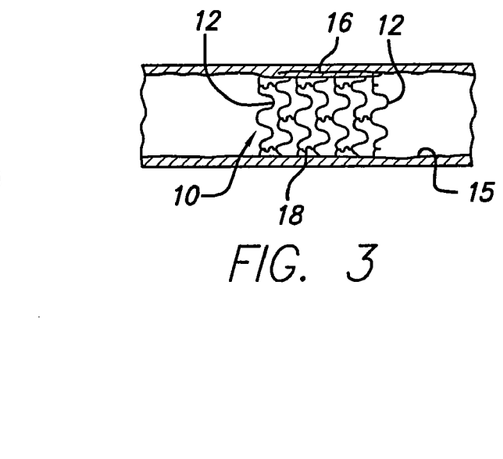
FIG. 3 is an elevational view, partially in section, depicting the expanded stent within the artery after withdrawal of the delivery catheter.

Referring now to FIGS. 2 and 3, once in position, the dilation balloon 14 is inflated to a predetermined size to radially expand the stent 10 against the inside of the artery wall and thereby implant the stent within the lumen of the artery 16. The balloon 14 is then deflated to a small profile so that the stent-delivery catheter may be withdrawn from the patient's vasculature and blood flow resumed through the artery.

The metallic cylindrical rings 12 of this embodiment are formed from tubular members and may be relatively flat in transverse cross-section. Thus, after implantation into the artery 16 as shown in FIG. 3, minimal interference with blood flow occurs. Eventually the stent becomes covered with endothelial cell growth, which further minimizes blood flow interference. As should be appreciated by those skilled in the art that, while the above-described procedure is typical, it is not the only method used in placing stents.

The stent patterns shown in FIGS. 1-3 are for illustration purposes only and can vary in size and shape to accommodate different vessels or body lumens. Further, the stent 10 is of a type that can be used in accordance with the present invention.

The polymeric links 18 which interconnect adjacent cylindrical rings 12 may have cross-sections similar to the cross-sections of the undulating components of the expandable cylindrical rings. The polymeric composition of the links may enable the links to be more flexible than comparatively sized metallic links. The number and location of the links connecting the rings together can be varied in order to vary the desired longitudinal and flexural flexibility in the stent assembly structure in the unexpanded as well as expanded condition of the stent. These properties are important to minimize alteration of the natural physiology of the body lumen into which the stent assembly is implanted and to maintain the compliance of the body lumen which is internally supported by the stent assembly. Generally, the greater the longitudinal and flexural flexibility of the stent assembly, the easier and the more safely it can be delivered to the target site.

Figure 4:
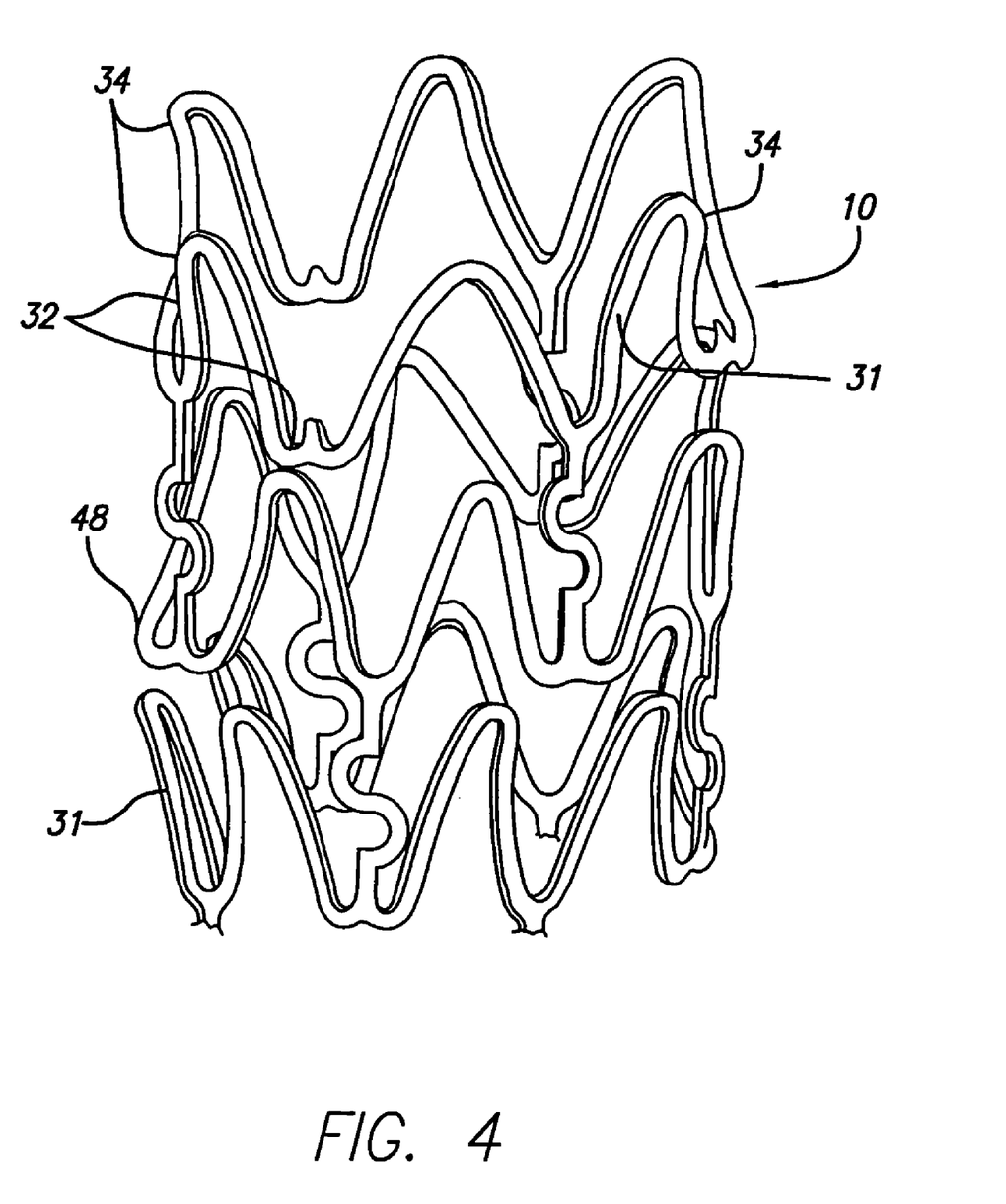
FIG. 4 is a perspective view of a portion of the stent of FIGS. 1-3 after it is fully expanded depicting some portions of the stent projecting radially outwardly.

With reference to FIG. 4, the stent 10 includes cylindrical rings 12 in the form of undulating portions. The undulating portions are made up of a plurality of U-shaped members 31 and W-shaped members 32 having radii that more evenly distribute expansion forces over the various members. Typically, the stent of the invention will not have discreet parts, however, u and w-shaped members are described for ease of reference. After the cylindrical rings have been radially expanded, outwardly projecting edges 34 may be formed. That is, during radial expansion some of the U- and W-shaped members may tip radially outwardly thereby forming outwardly projecting edges. These outwardly projecting edges can provide for a roughened outer wall surface of the stent and assist in implanting the stent in the vascular wall by embedding into the vascular wall. In other words, the outwardly projecting edges may embed into the vascular wall, for example arterial vessel 16, as depicted in FIG. 3. Depending upon the dimensions of the stent and the thickness of the various members making up the serpentine pattern, any of the U- or W-shaped members may tip radially outwardly to form the projecting edges.

The cylindrical rings 12 can be nested such that adjacent rings slightly overlap in the longitudinal direction so that one ring is slightly nested within the next ring and so on. The degree of nesting can be dictated primarily by the length of each cylindrical ring, the number of undulations in the rings, the thickness of the rings, and the radius of curvature, all in conjunction with the crimped or delivery diameter of the stent. If the rings are substantially nested one within the other, it may be difficult to crimp the stent to an appropriate delivery diameter without the various struts overlapping. It is also contemplated that the rings may be slightly nested even after the stent is expanded, which enhances vessel wall coverage. In some circumstances, it may not be desirable to nest one ring within the other, which is also contemplated by the invention.

Figure 5:
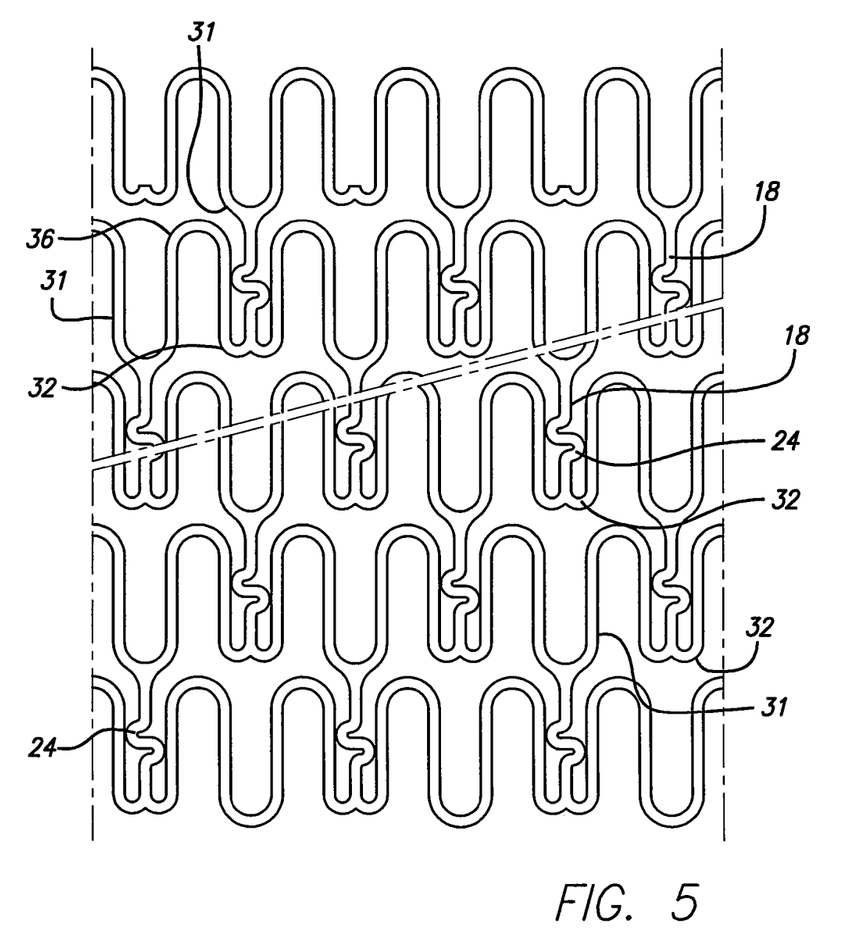
FIG. 5 is a plan view of a flattened section of the stent of the invention.

For the purpose of illustration only, the stent 10 is shown as a flat pattern in FIG. 5 so that the pattern of rings and links may be clearly viewed. Normally the stent of the present invention is formed of a cylindrical structure, however, it is beneficial to describe various parts to facilitate discussion. The rings 12 in the present embodiment have an undulating shape including peaks and valleys formed as U-shaped members 31 which are out of phase with the U-shaped members of adjacent cylindrical rings and W-shaped members 32 which are also out of phase with the W-shaped members of adjacent cylindrical rings. The particular pattern and how many undulations, or the amplitude of the undulations, are chosen to fill particular mechanical requirements for the stent, such as radial stiffness and longitudinal flexibility. Typically, each adjacent ring will be connected by at least one polymeric connecting link 18 and typically, each connecting link is circumferentially offset from the longitudinally preceding and succeeding connecting links. Generally, circumferentially offsetting the connecting links enhances uniform longitudinal flexibility of the stent, even though the links as shown are somewhat rigid. The number of cylindrical rings incorporated into the stent can also vary according to design requirements taking into consideration factors such as radial stiffness and longitudinal flexibility.

In keeping with the invention, the polymeric links 18 are formed from a flexible polymeric material, that is bendable and flexible to enhance longitudinal and flexural flexibility of the stent 10. The polymeric material forming the links can be taken from the group of polymers consisting of polyurethanes, polyolefins, polyesters, polyamides, fluoropolymers and their co-polymers, polyetherurethanes, polyesterurethanes, silicone, thermoplastic elastomer (C-flex), polyetheramide thermoplastic elastomer (Pebax), fluoroelastomers, fluorosilicone elastomer, polydimethyl siloxones (PDMS), aromatic PDMS, silicon thermoplastic urethanes, poly (glycerol sebacate) (PGS) (developed by Yadong Wang, MIT) and commonly referred to as biorubber) styrene-butadiene rubber, butadiene-styrene rubber, polyisoprene, neoprene (polychloroprene), ethylene-propylene elastomer, chlorosulfonated polyethylene elastomer, butyl rubber, polysulfide elastomer, polyacrylate elastomer, nitrile, rubber, a family of elastomers composed of styrene, ethylene, propylene, aliphatic polycarbonate polyurethane, polymers augmented with antioxidants, polymers augmented with image enhancing materials, polymers having a proton (H+) core, polymers augmented with protons (H+), butadiene and isoprene (Kraton), polyester thermoplastic elastomer (Hytrel), methacrylates, ethylene, acetate, alcohol, and polyvinyl alcohol. The polymeric links can also be translucent or radiopaque. In the case of a radiopaque link, the polymer may be modified with a radiopaque material.

The polymeric links can be formed with a curved pattern 24 to enable the stent to have higher flexibility and deliverability than a strut with substantially straight links. The links can also be formed in a number of different patterns according to design requirements. For example, the links can be formed with more or less surface area, larger or smaller cross-sections, variable radial thickness, a greater or lower number of curves or oscillations, and a variety of other shapes according to design requirements.

The polymeric links 18 when used in connection with the metallic cylindrical rings 12 enable the stent 10 to have higher flexibility and deliverability than all metal stents. The cylindrical rings are formed out of a metal, such as stainless steel and can be interconnected with the links through many types of connections including bonding agents, coatings and anchoring mechanisms. By comparison, an all metal stent generally consists of a series of metallic cylindrical rings interconnected by metallic links or struts. In the case of a metallic stent where the rings and links are laser cut from a unitary tube, the design of the stent may be a compromise between flexibility and rigidity, where the stent must be flexible enough to conform to the curvature of the body lumen it is inserted into and the stent must be rigid enough to remain in its expanded state once implanted.

In the stent of the present invention, the polymeric links 18 enable the stent 10 to exceed the longitudinal flexibility of conventional metallic stents made to similar dimensions. Such flexibility is achieved by factors such as choice of polymeric material, type of pattern, and desired final size. To account for the required radial strength, the cylindrical rings 12 are formed from a metallic material as in conventional metallic stents. Accordingly, it is possible with the present invention to produce a stent having radial strength equivalent to a conventional all-metallic stent while offering longitudinal flexibility exceeding the metallic stent. With the addition of more rings to the stent, radial stiffness can also be increased over a conventional stent while maintaining a high degree of flexibility.

The stent patterns shown in FIGS. 1-5 are for illustration purposes only and can vary in shape and size to accommodate different vessels or body lumens. Thus, rings 12 connected by links 18 can have any structural shapes and are not limited to the aforedescribed undulating rings including U- and W-shaped portions. Links connecting the rings can also include oscillating patterns, sinusoidal patterns and zig-zag patterns. One aspect of the invention provides for various anchoring mechanisms for attaching the links to the rings.

Figure 6:
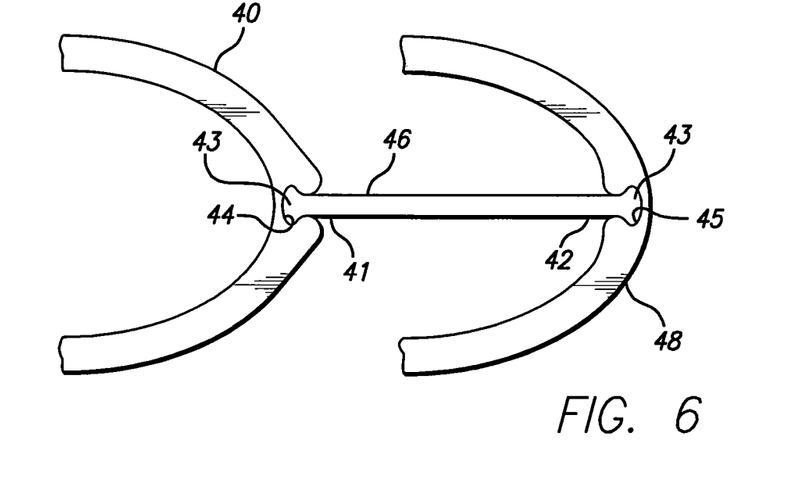
FIG. 6 is a plan view of a flattened section of a portion of two adjacent rings attached by one of the links.

As shown in FIG. 6, link 46 has a length which can vary, and connects a portion of one cylindrical ring 48 to a portion of adjacent cylindrical ring 40. The link has a first end 41, a second end 42 and locking heads 43 which one designed to fit within a correspondingly shaped first cavity 44 and second cavity 45, respectively. The polymer used to form the links is injection molded so that the locking heads can take any particular form in order to fill the first and second cavities.

Figure 7:
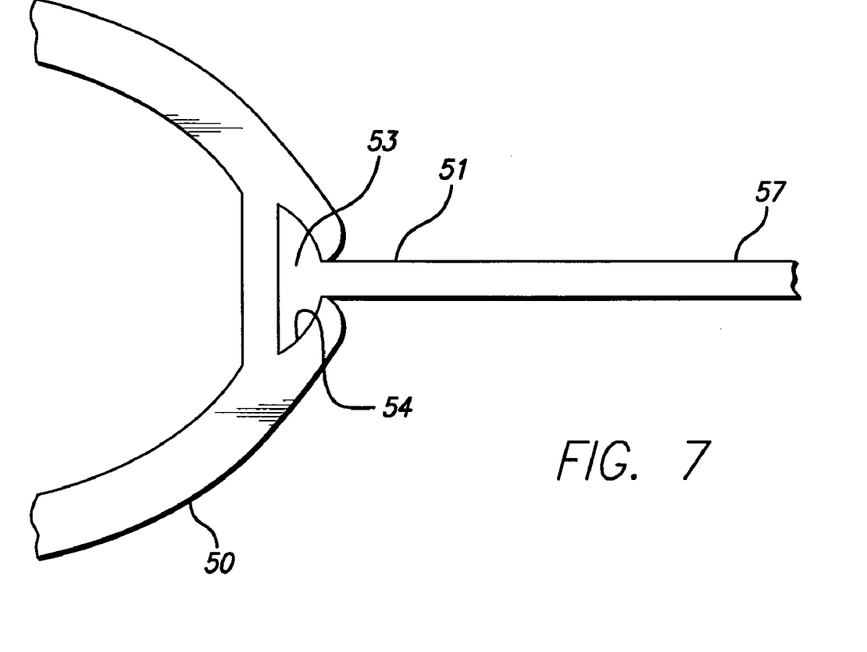
FIG. 7 is a plan view of a flattened section of one cylindrical ring of the stent and a link attached thereto.

An alternative link 57 is shown in FIG. 7, where the link has a first end 51 that is attached to a locking head 53 with a different shape than the locking head 43 shown in FIG. 6. In this figure, the opposite end of the link and the part of a ring that it is attached to has been omitted. The locking head corresponds to the shape of the first cavity 54 that has been machined into the apex of a portion of the cylindrical ring 50. Other shapes for locking heads and corresponding cavities are envisioned, and those shown in FIGS. 6 and 7 are for illustration purposes to show the interlocking relationship between the links and the cylindrical rings.

Figure 8:
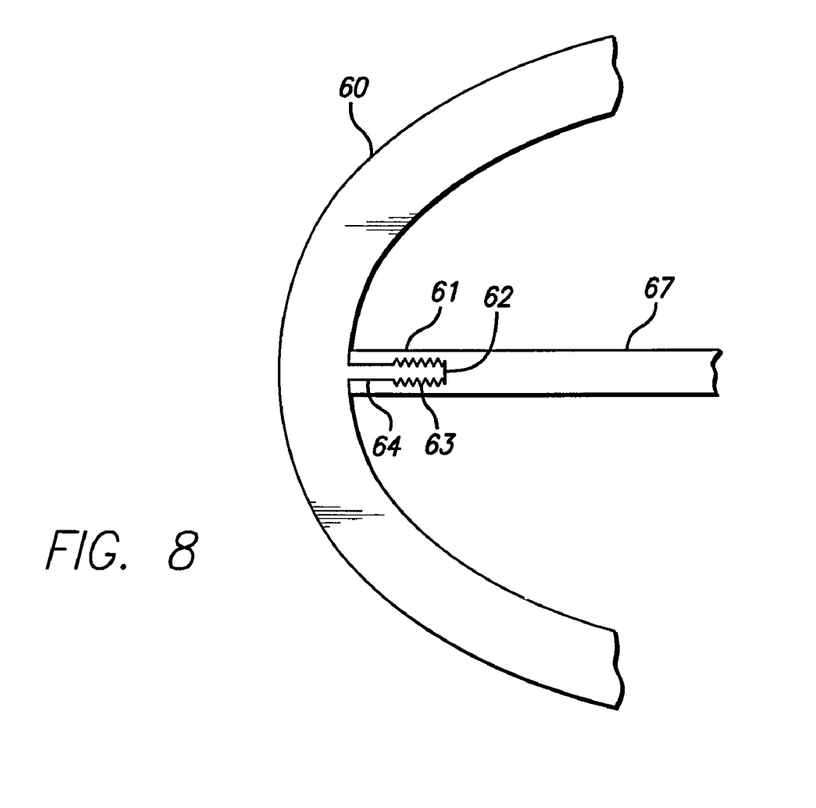
FIG. 8 is a plan view of a flattened section of one cylindrical ring with a link attached thereto.

In another embodiment, as shown in FIG. 8, a link 67 has a first end 61 that abuts a portion of a cylindrical ring 60. In this embodiment, the ring is formed with a locking head 62 which has a plurality of teeth 63 and a smooth portion shaft 64. The polymer link is either injection molded to surround or encapsulate the locking head or the portion surrounding the locking head is heated and the polymer link is pushed over the teeth and shaft portion of the locking head. As the structure cools, the polymer link becomes securely fastened to the locking head.

Figure 9:
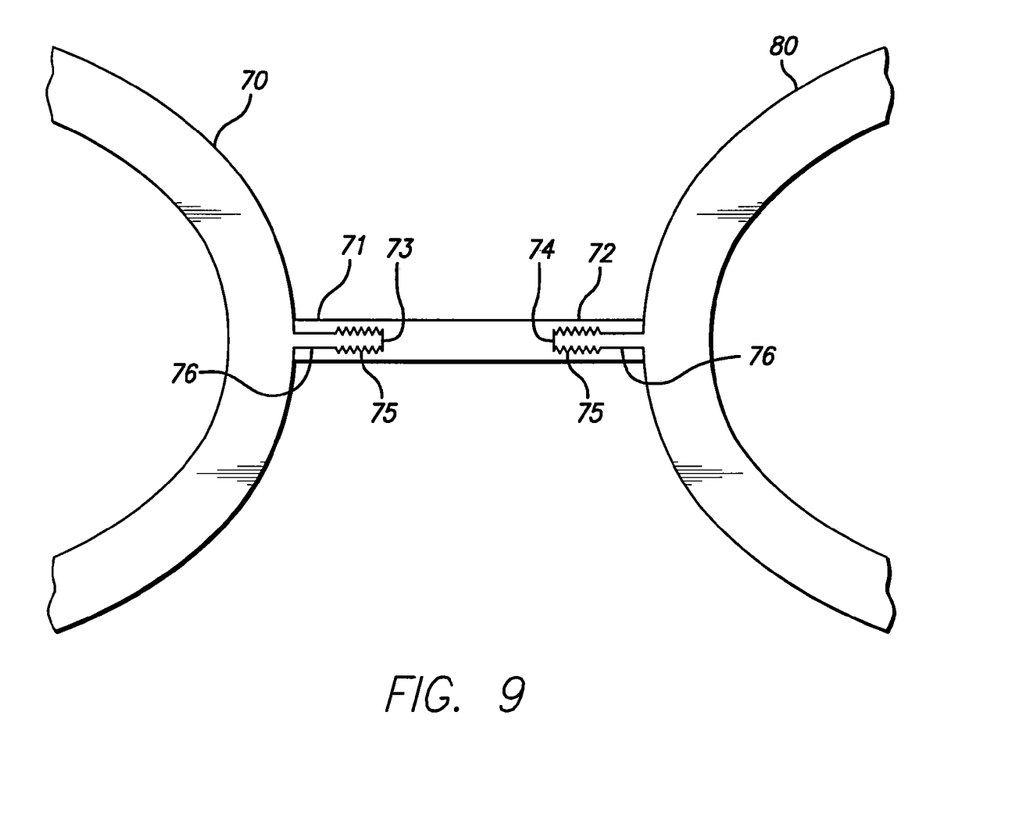
FIG. 9 is a plan view of a flattened section of a portion of two cylindrical rings with a link attached thereto.

In another embodiment shown in FIG. 9, a portion of a first ring 70 and a second ring 80 are connected by a link 78. The link has a first end 71 and a second end 72 which abuts peaks of the ring portions. The first end is attached to a first locking head 73 and the second end is attached to a second locking head 74. Each of the locking heads have teeth 75 for gripping the polymer link and a shaft 76. As described for the embodiment of FIG. 8, the polymer link can be injection molded or the locking heads may be heated and the polymer link pushed onto the locking heads and subsequently cooled to form the attachment.

Additional configurations are contemplated to increase the strength and reduce the profile of the polymer to metal attachment. Additional anchoring mechanisms that include geometric features designed to generate a lock and key type of fit may include hooks incorporated into either or both the links or rings whereby the links and rings are securely fastened together. In such cases the hooks can also be arranged in multiple fusion where the anchoring design specifies such an arrangement. The ring-to-link attachment can be accomplished in additional ways including using a bonding agent. For example, when using a bonding agent, adhesive can be applied at each end of the polymeric link and at corresponding rings. The adhesive can be any biocompatible adhesive that is well known, such as a cyanoacrylate-based adhesive. Several adhesives can be used including epoxy based adhesives, Locitite 401, 1-06FL, and M-11FL, the latter two of which are urethane-based adhesives. Other adhesives such as epoxy based adhesives can be used without departing from the spirit and scope of the invention. In addition, a coating applied to the entire stent can also be used to interconnect the links and rings.

The polymeric links may have cross-sections similar to the cross-sections of the undulating components of the expandable cylindrical rings. In one embodiment, the cross-section of the links may fall between approximately 0.0012 inch (0.03 mm) and 0.01 inch (0.25 mm). Compared to a conventional metallic link of similar size and shape, the polymeric link connecting adjacent rings provides increased flexibility to the stent by allowing adjacent rings to more freely conform to a patient's vasculature.

One method of making the rings is to laser cut the rings from a tubular member, such as stainless steel tubing to remove portions of the tubing in the desired pattern for the rings. Other possible ring materials include titanium, tantalum, nickel titanium, cobalt-chromium, gold, palladium, platinum and platinum-iridium. In accordance with the invention, it is preferred to cut the tubing in the desired pattern by means of a machine-controlled laser as is well known in the art.

Direct laser cutting produces edges which are essentially perpendicular to the axis of the laser cutting beam, in contrast with chemical etching and the like which produce pattern edges which are angled. Hence, the laser cutting process essentially provides stent cross-sections, from cut-to-cut, which are square or rectangular, rather than trapezoidal. The cross-sections have generally perpendicular edges formed by the laser cut.

Other methods of forming the rings of the present invention can be used, such as chemical etching; electric discharge machining; laser cutting a flat sheet and rolling it into a cylinder; and the like, all of which are well known in the art at this time.

Several processes can be used for forming and incorporating the polymeric links within the stent. One method is to first coat a core mandrel with a polymer coating.

Figures 10, 11, 11A:
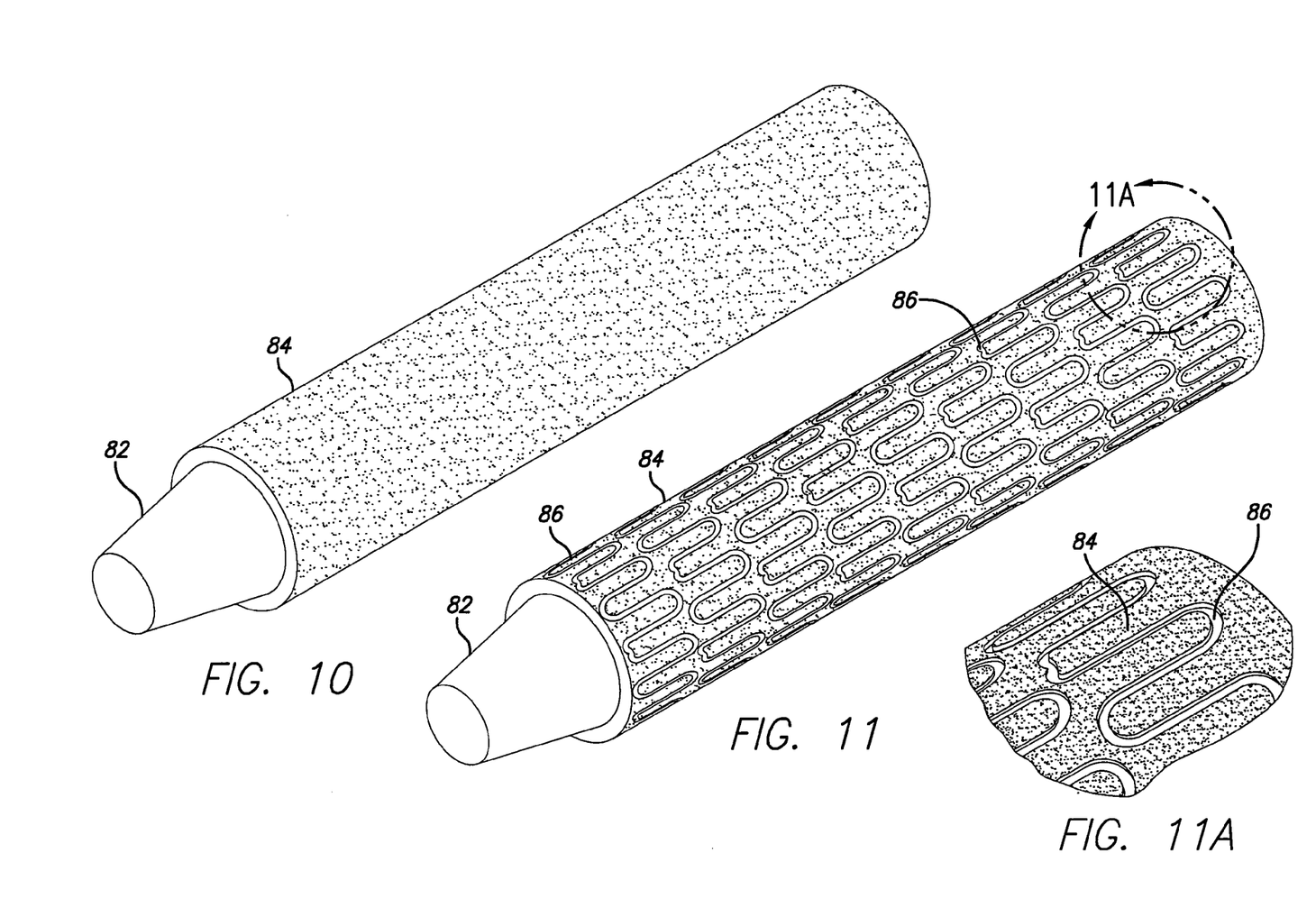
FIG. 10 is a perspective view of a mandrel coated with a polymer.
FIG. 11 is a perspective view of the mandrel of FIG. 10 depicting recesses for cylindrical rings.
FIG. 11A is an enlarged partial view of the stent recesses shown in FIG. 11.

In keeping with the invention, a mandrel 82 is shown in FIG. 10 coated with a polymer layer 84. The mandrel can be formed from solid stainless steel and have an outside diameter of approximately 0.100 inch (2.54 mm) to 0.105 inch (2.67 mm). The mandrel also can have a flat surface machined on a proximal end (not shown) in order to ensure that multiple laser processes could be registered to each other. The mandrel is coated with Elast-Eon II 80A (available from Aor Tech Biomaterials of Frenchs Forest, NSW, Australia) at a thickness in the range of approximately 0.003 (0.076 mm) to about 0.012 inch (0.254) to form a polymer layer. This layer is achieved by dissolving the Elast-Eon in DMAC (Dimethylacetamide) so that 2% by solids solution is made. In one embodiment, the mandrel is dipped three times with a two-hour cure at 80° C. occurring between dips. The dip extraction rate is approximately 2 to 7 inches/min (50.8 mm/min to 177.8 mm/min).

After curing the solution on the mandrel, a $CO_2$ laser (or Eximer lasers, solid state lasers and their harmonic wavelengths, picosecond lasers, or femtosecond lasers) is used to cut a ring cavity 86 into the polymer identical to the metallic rings of the stent. The cavity 86 is shown in FIG. 11 and in more detail in FIG. 11A including ring cavity 86. By way of example only, the $CO_2$ laser power and focus is adjusted so that the stent rings 12 may be fit snugly into the ring cavity of the layer and so that approximately 0.002 inch (0.051 mm) to 0.005 inch (0.127 mm) of the polymer is remaining under the ring cavity. The longitudinal length of each ring cavity is about 0.043 inch (1.1 mm). The spacing between ring cavities is about 0.004 inch (0.1 mm) apart so that fourteen to fifteen rings would generate a stent of about 8.709 inch (18 mm) in length. These lengths are for example only and are not meant to be limiting.

Figures 12, 13:
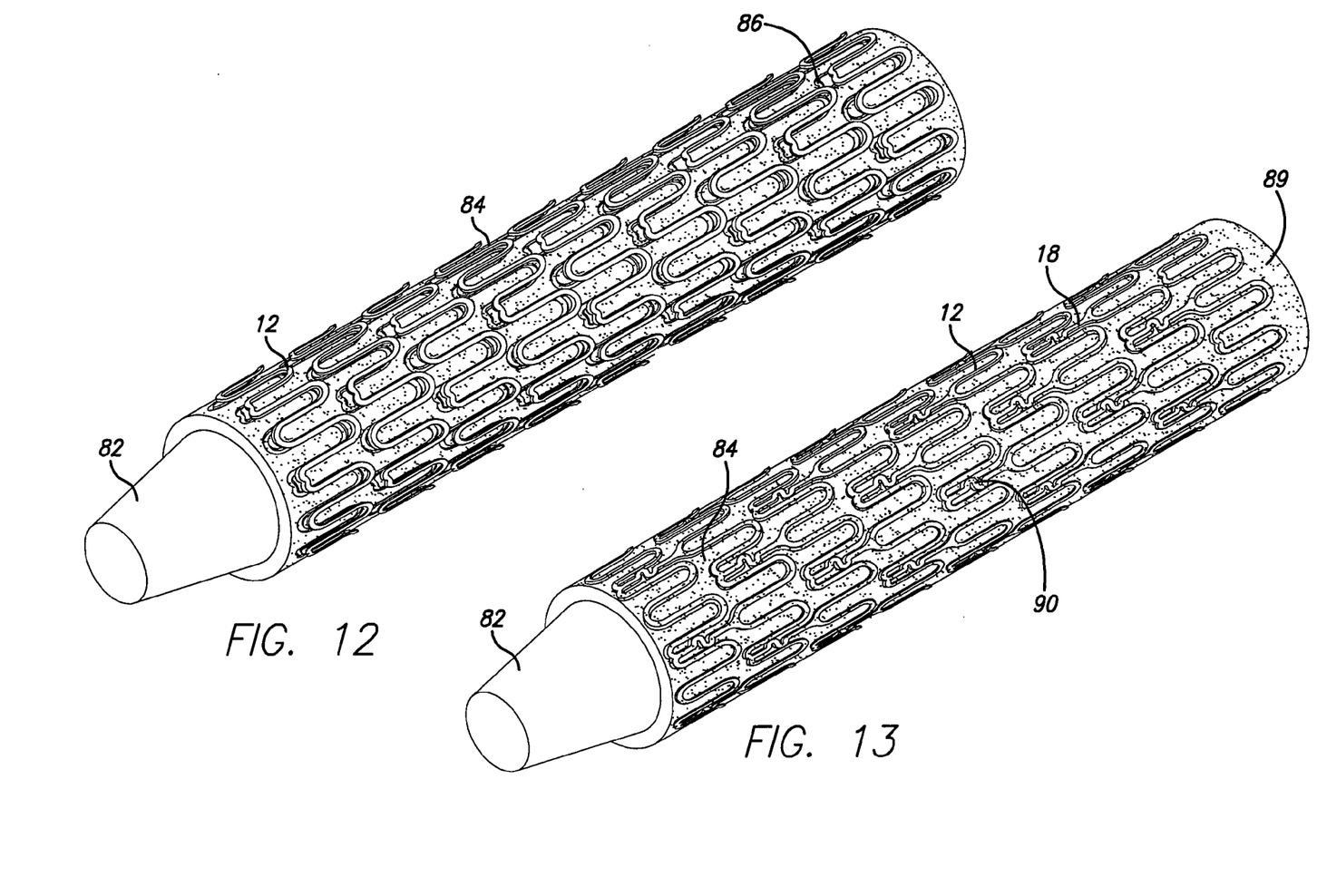
FIG. 12 is a perspective view of the mandrel of FIG. 10 and a series of cylindrical rings.
FIG. 13 is a perspective view of the stent after being formed on the mandrel.

After the stent rings 12 are cut (preferably by laser) they are pressed and crimped into the ring cavity 86 in the polymer layer 84. FIG. 12 shows the rings 12 before they are crimped onto the mandrel 82. Each ring 12 corresponds to the ring cavities 86 to form a tight fit. After the rings are inserted into the cavities 86, a final dip process is performed to coat the entire assembly including the stent rings 12 embedded in ring cavities 86. The thickness for the polymer coat 89 is preferably about 0.002 inch (0.051 mm) to 0.005 inch (0.127 mm). The $CO_2$ laser, using a second laser program, then cuts polymer islands in the form of links 90 into the assembly as shown in FIG. 13, much like the links seen in the conventional stent cutting process. After the polymer islands are cut, the islands may be manually picked out with tweezers or the process may be automated to cut the excess polymer away from the link.

The link to ring attachment strength of the stent can be further enhanced by increasing the surface area at the attachment location on a microscopic scale. The degree of surface roughness of the ring can vary from a mild surface etch to a more aggressive etch which creates pits which allows the polymer to flow into. Surface roughening/texturing is common for most materials including austenitic stainless steel and cobalt-chromium. These materials are particularly susceptible to corrosion of the grain boundaries and can be attacked with a variety of etchants such as $FeCl_3$ (ferric chloride), $CoCl_3$ (cobalt chloride), $NaS_2O_8$ (sodium persulfate), HCl (hydrochloric acid), etc. The grain boundaries are attacked causing larger grains to fall out and dissolve thereby forming a pit.

Reverse current process can also be used to remove material and make a surface texture on the rings. The surface texture can be formed at the specific attachment location for the purposes of enhancing the link to ring attachment strength. This can be done by applying a mask or resist on the rings and then selectively removing this mask thereby exposing the attachment locations. During the surface etching of the rings, the resist protects these areas of the rings where a polished surface finish is desired.

The stent of the present invention also can include a superelastic ring material. The term "superelastic" refers to an isothermal transformation, more specifically stress inducing a martensitic phase from an austenitic phase (commonly referred to as stress induced martensite). Alloys having superelastic properties generally have two phases: a martensitic phase, which has a relatively low tensile strength and which is stable at relatively low temperatures, and an austenitic phase, which has a relatively high tensile strength and which is stable at temperatures higher than the martensitic phase. The austenitic phase also typically has better corrosion properties. Superelastic characteristics generally allow the metal stent to be deformed by collapsing and deforming the stent and creating stress which causes the metal to change to the martensitic phase. The stent is restrained in the deformed condition to facilitate the insertion into a patient's body, with such deformation causing the phase transformation. Once within the body lumen, the restraint on the stent is removed, thereby reducing the stress therein so that the superelastic stent can return towards original undeformed shape by the transformation back to the austenitic phase. A basic discussion of this phenomenon can be found in Wayman and Deuring, "An Introduction to Martensite and Shape Memory," which appears in Engineering Aspects Of Shape Memory Alloys, Deuring et al. editors (Butterworth-Heinemann Ltd. 1990, Great Britain.)

The rings of the stent can be formed from a superelastic material such as NiTi (nickel titanium) and undergo an isothermal transformation when stressed. The stent is first compressed to a delivery diameter, thereby creating stress in the NiTi alloy so that the NiTi is in a martensitic state having relatively low tensile strength. While still in the martensitic phase, the stent is mounted onto or within a catheter by known methods.

In another embodiment, the stent may also be coated with a therapeutic agent to perform a variety of functions, from preventing blood clots to promoting healing. As an example, an active agent coated on the stent can inhibit the activity of vascular smooth muscle cells. More specifically, the active agent is aimed at inhibiting abnormal or inappropriate migration and proliferation of smooth muscle cells. The active agent can also include any substance capable of exerting a therapeutic or prophylactic effect in the practice of the present invention. The agent can also be for enhancing wound healing in a vascular site or improving the structural and elastic properties of the vascular site. The dosage or concentration of the active agent required to produce a favorable therapeutic effect should be less than the level at which the active agent produces toxic effects and greater than the level at which nontherapeutic results are obtained. The dosage or concentration of the active agent required to inhibit the desired cellular activity of the vascular region can depend upon factors such as the particular circumstances of the patient; the nature of the trauma; the nature of the therapy desired; the time over which the ingredient administered resides at the vascular site; and if other therapeutic agents are employed, the nature and type of the substance or combination of substances. Therapeutic effective dosages can be determined empirically, for example by infusing vessels from suitable animal model systems and using immunohistochemical, fluorescent or electron microscopy methods to detect the agent and its effects, or by conducting suitable in vitro studies. Standard pharmacological test procedures to determine dosages are understood by one of ordinary skill in the art.

Further, it is well known that the stent (when made from a metal) may require a primer material coating such as a polymer to provide a substrate on which a drug or therapeutic agent is coated since some drugs and therapeutic agents do not readily adhere to a metallic surface. The drug or therapeutic agent can be combined with a coating or other medium used for controlled release rates of the drug or therapeutic agent. Examples of therapeutic agents or drugs that are suitable for use with the polymeric materials include sirolimus, everolimus, actinomycin D (ActD), taxol, paclitaxel, or derivatives and analogs thereof. Examples of agents include other antiproliferative substances as well as antineoplastic, antiinflammatory, antiplatelet, anticoagulant, antifibrin, antithrombin, antimitotic, antibiotic, and antioxidant substances. Examples of antineoplastics include taxol (paclitaxel and docetaxel). Further examples of therapeutic drugs or agents that can be combined with the polymeric materials include antiplatelets, anticoagulants, antifibrins, antithrombins, and antiproliferatives. Examples of antiplatelets, anticoagulants, antifibrins, and antithrombins include, but are not limited to, sodium heparin, low molecular weight heparin, hirudin, argatroban, forskolin, vapiprost, prostacyclin and prostacyclin analogs, dextran, D-phe-pro-arg-chloromethylketone (synthetic antithrombin), dipyridamole, glycoprotein IIb/IIIa platelet membrane receptor antagonist, recombinant hirudin, thrombin inhibitor (available from Biogen located in Cambridge, Mass.), and 7E-3B® (an antiplatelet drug from Centocor located in Malvern, Pa.). Examples of antimitotic agents include methotrexate, azathioprine, vincristine, vinblastine, fluorouracil, adriamycin, and mutamycin. Examples of cytostatic or antiproliferative agents include angiopeptin (a somatostatin analog from Ibsen located in the United Kingdom), angiotensin converting enzyme inhibitors such as CAPTOPRIL® (available from Squibb located in New York, N.Y.), CILAZAPRIL® (available from Hoffman-LaRoche located in Basel, Switzerland), or LISINOPRIL® (available from Merck located in Whitehouse Station, N.J.); calcium channel blockers (such as Nifedipine), colchicine, fibroblast growth factor (FGF) antagonists, fish oil (omega 3-fatty acid), histamine antagonists, LOVASTATIN® (an inhibitor of HMG-CoA reductase, a cholesterol lowering drug from Merck), methotrexate, monoclonal antibodies (such as PDGF receptors), nitroprusside, phosphodiesterase inhibitors, prostaglandin inhibitor (available from GlaxoSmithKline located in United Kingdom), Seramin (a PDGF antagonist), serotonin blockers, steroids, thioprotease inhibitors, triazolopyrimidine (a PDGF antagonist), and nitric oxide. Other therapeutic drugs or agents which may be appropriate include alpha-interferon, genetically engineered epithelial cells, and dexamethasone.

While the invention has been illustrated and described herein in terms of its use as an intravascular stent, it will be apparent to those skilled in the art that the stent can be used in other body lumens. Further, particular sizes and dimensions, number of undulations per ring, materials used, and the like have been described herein and are provided as examples only. Other modifications and improvements may be made without departing from the scope of the invention.

What is claimed:

1. A method for forming an intravascular stent, comprising:
    forming a plurality of metallic cylindrical rings;
    coating a mandrel with a first series of polymeric layers;
    forming a plurality of cylindrical ring cavities in the polymeric layers;
    embedding the cylindrical rings into the cylindrical ring cavities;
    coating the cylindrical rings and first polymeric layers with a second series of polymeric coatings;
    ablating the first polymeric layers and the second polymeric coatings to form a stent.

2. The method of claim 1, wherein forming a plurality of metallic cylindrical rings comprises laser cutting the cylindrical rings.

3. The method of claim 1, wherein the cylindrical rings cavities are sized to conform with the cylindrical rings.

4. The method of claim 3, wherein a laser forms the cylindrical ring cavities in the first polymeric layers.

5. The method of claim 1, wherein the first series of polymeric layers is applied in a thickness approximately equal to the thickness of the cylindrical rings.

6. The method of claim 1, wherein the mandrel incorporates laser registration features.

7. The method of claim 6, wherein the coated mandrel is removed from a laser rotary fixture with its position registered in a control memory after forming a plurality of cylindrical ring cavities.

8. The method of claim 7, wherein the coated mandrel is placed back into the laser rotary fixture after coating the cylindrical rings and first polymeric layers with a second series of polymeric coatings.

9. The method of claim 8, wherein the coated mandrel is cured after coating the cylindrical rings and polymeric layers with a second series of polymeric coatings.

10. The method of claim 1, wherein forming a plurality of cylindrical rings cavities comprises laser cutting the cavities into the polymeric layers so that at least of some of the first polymer layers remains on the mandrel.

11. The method of claim 1, wherein the laser is any of a CO2 laser, an Eximer laser, or solid state laser, picosecond laser, or femtosecond laser.

* * * * *

UNITED STATES PATENT AND TRADEMARK OFFICE
CERTIFICATE OF CORRECTION

| | |
|---|---|
| PATENT NO. | : 7,645,409 B2 |
| APPLICATION NO. | : 12/245420 |
| DATED | : January 12, 2010 |
| INVENTOR(S) | : Richard J. Saunders et al. |

It is certified that error appears in the above-identified patent and that said Letters Patent is hereby corrected as shown below:

Column 7, line 54, after "43" delete "which" and insert instead --with--.

Column 12, line 29, after "cylindrical" delete "rings" and insert instead --ring--.

Column 12, line 50, after "cylindrical" delete "rings" and insert instead --ring--.

Column 12, line 51, after "least" delete "of".

Column 12, line 52, after "layers" delete "remains" and insert instead --remain--.

Signed and Sealed this
Eleventh Day of September, 2012

David J. Kappos
*Director of the United States Patent and Trademark Office*